(12) United States Patent
DiMauro et al.

(10) Patent No.: US 7,939,078 B2
(45) Date of Patent: May 10, 2011

(54) METHODS OF ENHANCING THE IMMUNE RESPONSE TO AUTOANTIGENS IN MUCOSAL ASSOCIATED LYMPHATIC TISSUE

(75) Inventors: Thomas M. DiMauro, Southboro, MA (US); Mohamed Attawia, Canton, MA (US); Sean Lilienfeld, Sharon, MA (US); Chantal Holy, Raynham, MA (US)

(73) Assignee: Codman & Shurtleff, Raynham, MA (US)

( * ) Notice: Subject to any disclaimer, the term of this patent is extended or adjusted under 35 U.S.C. 154(b) by 985 days.

(21) Appl. No.: 11/176,437

(22) Filed: Jul. 7, 2005

(65) Prior Publication Data

US 2007/0010859 A1    Jan. 11, 2007

(51) Int. Cl.
*A61K 38/17*    (2006.01)
*A61N 5/06*    (2006.01)

(52) U.S. Cl. .................... 424/184.1; 514/12.2; 514/21.2; 607/88

(58) Field of Classification Search ........................ None
See application file for complete search history.

(56) References Cited

U.S. PATENT DOCUMENTS

| | | | |
|---|---|---|---|
| 4,838,852 | A | 6/1989 | Edelson |
| 5,935,577 | A | 8/1999 | Weiner |
| 6,068,844 | A | 5/2000 | Becker |
| 6,645,504 | B1 | 11/2003 | Weiner |
| 7,226,470 | B2 | 6/2007 | Kemeny |
| 7,261,896 | B2 | 8/2007 | Hallenbeck |
| 2004/0009125 | A1* | 1/2004 | Hallenbeck et al. ............ 424/45 |
| 2004/0030368 | A1 | 2/2004 | Kemeny |
| 2004/0204747 | A1* | 10/2004 | Kemeny et al. ................ 607/94 |
| 2006/0292182 | A1* | 12/2006 | Kemeny et al. ............ 424/275.1 |
| 2008/0107663 | A1 | 5/2008 | Groux |

OTHER PUBLICATIONS

Cooper et al. PNAS(USA), vol. 89, pp. 8497-8501, 1992.*
van Kempen et al. Int. Arch. Alllergy Immunol., vol. 122, pp. 8-19, 2000.*
Csoma et al. J. Photochem. Photobiol. B: Biology, 2004, vol. 75, pp. 137-144.*
Takeda et al. Stroke, 2002, vol. 33, pp. 2156-2164.*
Mallat, "Induction of a Regulatory T Cell Type I Response Reduces the Development of Atherosclerosis in Apolipoprotein E-Knockout Mice", Basic Science Reports, Circulation, 2003, pp. 1232-1237, vol. 108, American Heart Association.
Barbey, "Intranasal Treatment With Ovalbumin Cut Not The Major T Cell Epitope Ovalbumin 323-339 Generates Interleukin-10 Secreting T Cells And Results In The Induction of Allergen Systemic Tolerance", Clinical & Experimental Allergy, 2004, pp. 654-62, vol. 34, Issue 4, Blackwell Publishing Ltd.
Ghoreishi, "Tolerance Induction by Transcutaneous Immunization through Ultraviolet-Irradiated Skin Is Transferable through CD4+CD25+ T Regulatory Cells and Is Dependent on Host-Derived IL-10", The Journal of Immunology, 2006, pp. 2635-2644, vol. 176. The American Association of Immunologists.
Schwarz, "Mechanisms of UV-induced Immunosuppression", Keio Journal of Medicine, 2005, pp. 165-171, vol. 54 (4), Dept. of Dermatology, University Kiel, Germany.
Ullrich, "Mechanisms Underlying UV-induced Immune Suppression", Mutation Research 571, 2005, pp. 185-205, Elservier B.V.
Beissert, "Regulatory T Cells", Journal of Investigative Dermatology, 2006, pp. 15-24, vol. 126, Society for Investigative Dermatology.
Weiner, "Oral Tolerance: Immune Mechanisms and the generation of Th3-type TGF-beta-secreting Regulatory Cells", Microbes and Infection, 2001, pp. 947-954, Elsevier.
Chen, "Regulatory T Cell Clones Induced by Oral Tolerance: Suppressiono f Autoimmune Encephalomyelitis", Science, Aug. 1994, pp. 1237-1240, vol. 265 (abstract only).
Hernandez-Pando, "The role of TNF-a in T-cell-mediated Inflammation Depends on the Th1/Th2 Cytokine Balance", Immunology, Aug. 1994, pp. 591-595, vol. 82(4), Dept. of Medical Microbiology, UCL Med School, London, UK.
Nagler, "Oral Tolerization Ameliorates Liver Disorders Associated With Chronic Graft Versus Host Disease in Mice", Hepatology, Mar. 2000, pp. 641-648, vol. 31(3), American Association for the Study of Liver Diseases.
Slavin, "Mucosal Administration of IL-10 Enhances Oral Tolerance in Autoimmune Encephalomyelitis and Diabetes", International Immunology, pp. 825-833, vol. 13(6), Japanese Society for Immunology. 2001 .
Inobe, "IL-4 is a Differentiation Factor for Transforming Growth Factor-B secreting Th3 Cells and Oral Administration of IL-4 Enhances Oral Tolerance in Experimental Allergic Encephalomyelitis", Eur. J. Immunol. 1998, pp. 2780-2790, vol. 28, Wiley-VCH Verlag GmbH, Weinheim.
Magee, Suppression Of The Elicitation Of The Immune Response to Alloantigen by Ultraviolet Radiation, Transplantation, Jun. 1989, pp. 1008-1013, vol. 47, The Williams & Wilkins Co.
Ullrich, "Does Exposure to UV Radiation Induce a Shift to a Th-2-like Immune Reaction?", Photochemistry and Photobiology, 1996, pp. 254-258, vol. 64(2), American Society for Photobiology.
Ullrich, Specific Suppression Of Allograft Rejection After Treatment Of Recipient Mice With Ultraviolet Radiation And Allogeneic Spleen Cells:, Transplantation, Jul. 1998, pp. 115-119, vol. 46 No. 1, The Williams & Wilkins Co.
Csoma, "Intranasal Irradiation With The Xenon Chloride Ultraviolet B Laser Improves Allergic Rhinitis", Journal of Photochemistry and Photobiology B: Biology, 2004, pp. 137-144, vol. 75, Elsevier B.V.
Liu, "Dendritic Cell Lineage, Plasticity and Cross-regulation", Nature Immunology, Jul. 2001, pp. 585-589, vol. 2 No. 7, Nature Publishing Group.

(Continued)

*Primary Examiner* — Jeffrey Stucker
*Assistant Examiner* — Stephen Gucker
(74) *Attorney, Agent, or Firm* — Thomas M. DiMauro

(57) ABSTRACT

Co-administration of an effective amount of autoantigen and UV light to mucosal associated lymphatic tissue (MALT) in a patient.

4 Claims, No Drawings

OTHER PUBLICATIONS

King, "TGF-B1 Alters APC Preference, Polarizing Islet Antigen Responses toward a Th2 Phenotype", Immunity, May 1998, pp. 601-613, vol. 8, Cell Press.

Mattsson, "Immunization with Alum—Collagen II Complex Suppresses the Development of Collagen-Induced Arthritis in Rats by Deviating the Immune Response", Scand. J. Immunol., 1997, pp. 619-624 vol. 46, Blackwell Science Ltd.

Brewer, "Aluminium Hydroxide Adjuvant Initiates Strong Antigen-Specific Th2 Responses in the Absence of IL-4- or IL-13-Mediated Signaling1", J. Immunology, 1999, pp. 6448-6454, vol. 163, The American Association of Radiologist.

Comoy, "In Vivo Induction Of Type 1 And 2 Immune Responses Against Protein Antigens", International Immunology, 1997, pp. 523-531, vol. 9, No. 4, Oxford University Press.

Cribbs, "Adjuvant-dependent Modulation of Tn1 and Tn2 Responses to Immunization with B-amyloiid", International Immunology, 2003, pp. 505-514, vol. 15, No. 4, The Japanese Society for Immunology.

Becker, "Adoptive Transfer of Myelin Basic Protein-Tolerized Splenocytes to Naive Animals Reduces Infarct Size—A Role for Lymphocytes in Ischemic Brain Injury?", Stroke, 2003, pp. 1809-1815, American Heart Association.

Stohlman, "Activation of Regulatory Cells Suppresses Experimental Allergic Encephalomyelitis Via Secretion of IL-10", The Journal of Immunology, 1999, pp. 6338-6344; vol. 163., The American Association of Immunologists.

Frenkel, "Nasal Vaccination with Myelin Oligodendrocyte Glycoprotein Reduces Stroke Size by Inducing IL-10-Producing CD4+ T Cells", The Journal of Immunology, 2004, pp. 6549-6555, vol. 172, The American Association of Immunologists, Inc.

Takeda, "Induction of Mucosal Tolerance to E-Selectin Prevents Ischemic and Hemorrhagic Stroke in Spontaneously Hypertensive Genetically Stroke-Prone Rats", Stroke, Sep. 2002, pp. 2156-64, vol. 33, American Heart Association.

Viac, "Effect of UVB 311 nm Irradiation on Normal Human Skin", Photodermatol. Photoimmunol. Photomed., Jun. 1997, pp. 103-108, vol. 13(3), Clinique Dermatologique, Lyon France (abstract only).

Heckman,"Ultraviolet-A Radiation Induces Adhesion Molecule Expression On Human Dermal Microvascular Endothelial Cells", Br. J. Dermatol., Sep. 1994, p. 311-318, vol. 131(3), (UVA), The Society for Investigative Dermatology (abstract only).

Schornagel, "Decreased Neutrophil Skin Infiltration After UVB Exposure in Patients with Polymorphous Light Eruption", The Journal of Investigative Dermatology, 2004, pp. 202-206, vol. 123, The Society for Investigative Dermatology, Inc.

Strickland, TNF-a and IL-8 Are Upregulated in the Epidermis of Normal Human Skin after UVB Exposure: Correlation with Neutrophil Accumulation and E-Selectin Expression:, The Journal of Investigative Dermatology, May 1997, pp. 763-768, vol. 108(5). The Society of Investigative Dermatology, Inc.

Norris, "The Expression of Endothelial Leukocyte Adhesion Molucule-1 (ELAM-1), Intercellular Adhesion Molecule 1 (ICAM-1), and Vascular Cell Adhesion Molecule-1 (VCAM-1) in Experimental Cutaneous Inflammation: A Comparison of Ultraviolet B Erythema and Delayed Hypersensitivity", The Journal of Investigative Dermatology, 1991, pp. 763-770, vol, 96, The Society for Investigative Dermatology, Inc.

Rahman, "E-selectin Expression in Human Endothelial Cells by TNF-a-induced Oxidant Generation and NF-kB Activation", American Journal of Physiology (Lung Cell. Mol. Physiol. 19), 1998, pp. L533-L544, the American Physiological Society.

Weiner, "Nasal Administration of Amyloid-B Peptide Decreases Cerebral Amyloid Burden in a Mouse Model of Alzheimer's Disease", Annals of Neurology, Oct. 2000, pp. 567-579, vol. 48(4), American Neurological Association.

Maron, "Regulatory Th2 type T cell Lines Against Insulin and GAD Peptides Derived from Orally- and Nasally-Treated Nod Mice Suppress Diabetes", Journal of Autoimmunity, 1999, pp. 251-258, vol. 12, Academic Press.

Shreedhar, "A Cytokine Cascade Including Prostaglandin E2, IL-4, and IL-10 Is Responsible for UV-Induced Systemic Immune Suppression", The Journal of Immunology, 1998, pp. 3783-9 vol. 160, The American Association of Immunologists.

Schmitt, "Exposure to Ultraviolet Radiation Causes Dendritic Cells/Macrophases to Secrete Immune-Suppressive IL-12p40 Homodimers", The Journal of Immunology, 2000, pp. 3162-3167, vol. 165, The American Association of Immunologists.

Rivas, "Systemic Suppression of Delayed-Type Hypersensitivity by Supernatants From UV-Irradiated Keratinocytes—An Essential Role for Keratinocyite-Derived IL-10", The Journal of Immunology, Dec. 15, 1992, pp. 3865-3871, vol. 149, No. 12, The American Association of Immunologists.

Kang, "CD11 b+ Macrophages That Infiltrate Human Epidermis After In Vivo Ultraviolet Exposure Potently Produce IL-10 and Represent the Major Secretory Source of Epidermal IL-10 Proteinl" J. Immunol., 1994, pp. 5256-5264, vol. 153, The American Association of Immunologists.

Ikezawa, "Characterization of Cementum Derived Growth Factor as an Insulin-like Growth Factor-I like Molecule", Conn. Tiss. Res., 1997, pp. 309-319, vol. 36(4) (abstract only).

Mangrulkar, "Isolation and Characterization of Heparin-Binding Growth Factors in Human Leiomyomas and Normal Myometrium", Biology of Reproduction, 1995, pp. 636-646, vol. 53.

Sakurada, "Involvement of Vascular Endothelial Growth Factor in Kaposi's Sarcoma Associated with Acquired Immunodeficiency Syndrome", Japan Journal of Cancer Research, Nov. 1996, pp. 1143-1152, vol. 87(11) (abstract only).

McCaffrey, "Transforming Growth Factor-beta 1 is a Heparin-binding Protein: Identification of Putative Heparin-binding Regions and Isolation of Heparins with Varying Affinity for TGF-beta 1", Journal of Cell Physiology, Aug. 1992, pp. 430-440, vol. 152(2) (abstract only).

Ossevoort, "A Rapid Isolation Procedure for Dendritic Cells From Mouse Spleen by Centrifugal Elutriation", J. Immunol. Methods, 1992, pp. 101-111, vol. 155 (abstract only).

Weiner, "Double-blind Pilot Trial of Oral Tolerization with Myelin Antigens in Multiple Sclerosis", Science,1993, pp. 1321-1324, vol. 259 (abstract only).

Trentham, "Effects of Oral Administration of Type II Collagen on Rheumatoid Arthritis", Science, 1993, pp. 1727, vol. 261 (abstract only).

Arora, "The Role of Th1 and TH2 Immune Responses in Loosening and Osteolysis of Cemented Total Hip Replacements", JBMR, 2003, pp. 693-697, vol. 64A (abstract only).

Cooper, "UV Exposure Reduces Immunization Rates and Promotes Tolerance to Epicutaneous Antigens in Humans: Relationship to Dose, CD1a-DR+ Epidermal Macrophage Induction, and Langerhans Cell Depletion"; Immunology, PNAS, Sep. 1992; pp. 8497-8501; vol. 89.

Van Kempen et al., "The Immune Response in Adenoids and Tonsils"; Int Arch Allergy Immunol; May 2000; pp. 8-19; vol. 122 (abstract only).

* cited by examiner

METHODS OF ENHANCING THE IMMUNE RESPONSE TO AUTOANTIGENS IN MUCOSAL ASSOCIATED LYMPHATIC TISSUE

BACKGROUND OF THE INVENTION

Bystander suppression involves mucosal administration of antigens specific to a tissue under autoimmune attack.

Mucosal administration of certain antigens causes suppressor T-cells to be induced in mucosa-associated lymphoid tissue (MALT). These antigen-specific suppressor T-cells are released in the blood or lymphatic tissue and then migrate to the organ or tissue afflicted by the autoimmune disease (which has a high concentrated of the antigen). Once they have arrived at their intended target, these suppressor T-cells mediate the release of immunosuppressive cytokines such as transforming growth factor β (TGF-β), IL-4 and/or IL-10 and thereby suppress autoimmune attack of the afflicted organ or tissue.

In more detail, the mechanism of bystander suppression is as follows: After a tissue-specific bystander antigen is mucosally administered, it passes to local lymph tissue (such as Peyers Patches in the gut), which contain T cells and B cells. These cells, are in turn in communication with the immune system, including the spleen and lymph nodes. The result is that suppressor (CD8+) T-cells are induced and recruited to the area of autoimmune attack, where they cause the release of TGF-β, IL-4 and IL-10, which can non-specifically down-regulate the B-cells as well as the activated CD4+T-cells directed against the mammal's own tissues. Despite the non-specific nature of the activity of these cytokines, the resulting tolerance is specific for the autoimmune disease by virtue of the fact that the antigen is specific for the tissue under attack and suppresses the immune cells that are found at or near the tissue being damaged.

TGF-B is an anti-inflammatory cytokine that helps polarize the immune response towards a Th2 phenotype. IL-4 and IL-10 are also antigen-nonspecific immunoregulatory cytokines. IL-4 in particular enhances Th2 response, i.e., acts on T-cell precursors and causes them to differentiate preferentially into Th2 cells at the expense of Th1 responses. IL-4 also indirectly inhibits Th1 exacerbation. IL-10 is a direct inhibitor of Th1 responses. After orally tolerizing mammals afflicted with autoimmune disease conditions with bystander antigens, increased levels of TGF-β, IL-4 and IL-10 are observed at the locus of autoimmune attack. Chen, Y. et al., *Science*, 265:1237-1240, 1994.

The action of these cytokines is not specific for the antigen triggering the suppressor cells that release them, even though these suppressor T-cells release these cytokines only when triggered by the mucosally-administered antigen. However, because mucosal tolerization with the antigen only causes the release of these cytokines in the vicinity of autoimmune attack, no systemic immunosuppression ensues. Recruitment of the suppressor T-cells to a locus where cells contributing to the autoimmune destruction are concentrated allows for the release of these suppressive cytokines in the vicinity of the disease-causing cells and suppresses (i.e. shuts down) these cells. The ability of these immunosuppressive cytokines to suppress these "destructive" cells is independent of the antigen for which the destructive cells may be specific.

U.S. Pat. No. 6,645,504 ("Weiner I") and U.S. Pat. No. 5,935,577 ("Weiner II") each discloses that certain synergists can be co-administered along with the antigen to enhance the effectiveness of the tolerance-promoting treatment. Particularly, noted is the use of IL-4; IL-10; bacterial lipopolysaccharides; immunoregulatory lipoproteins; and cholera toxin β-chain (CTB).

SUMMARY OF THE INVENTION

The present inventors have developed inventions whereby mucosal tolerance of an antigen is enhanced by UV irradiation.

Mucosal tolerance to low dose (typically, 1 ng to 10 g) antigens involves the induction of cells that actively suppress Th1-type responses to those antigens. However, because a properly functioning immune system generally relies upon a balance of Th1 and Th2 phenotypes, the natural mucosal response to an antigen may be a mixture of Th1 and Th2 responses—not a pure polarization. See, for example, mixed Th1/Th2 responses reported in Hernandez-Pando, *Immunology*, 1994, Aug. 82(4) 591-5 and Nagler, *Hepatology*, 2000, Mar. 31(3) 641-8, and Arora, *JBMR* 64A:693-697, 2003.

Since it is likely that an antigen-driven immune response in mucosal tissue likewise invokes a mixed type immune response involving both Th1 and Th2 cells and both pro- and anti-inflammatory cytokines, the present inventors believe there may be a significant Th1 component in the immune response even when low dose antigens are contacted with mucosal tissue such as nasal associated lymphatic tissue (NALT). Accordingly, factors that favor the induction of Th2 cells should enhance low dose mucosal tolerance of antigens.

Therefore, in some embodiments, the present invention relates to co-administration of an effective amount of antigen and UV light to mucosal associated lymphatic tissue (MALT) in a patient.

Without wishing to be tied to a theory, it is believed that UV light irradiation of the MALT will enhance the Th2 response to antigens in two ways.

First, the UVB light irradiation will cause local production of IL-10 in the MALT. It has been reported in the literature that irradiation of skin with UVB light causes the release of IL-10 and prostaglandin by keratinocytes. The induced prostaglandin in turn induces the release of IL-4 and more IL-10 by macrophages recruited to the irradiated region.

The IL-10 produced by this irradiation will enhance tolerance to the co-administered antigen that has been delivered to the MALT. It has been shown by Slavin, *International Immunology*, 13(6) 825-833 that adding IL-10 to nasally administered MBP enhances the Th2 response that produces tolerance to autoimmune encephalomyelitis. Similarly, Inobe, *Eur. J. Immunol.* 1998, 28, 2780-90 reports that mucosal (oral) administration of IL-4 enhances tolerance to MBP in experimental allergic encephalomyelitis (EAE).

Second, the UVB light irradiation will effect the local antigen presentation within the MALT. Generally, Ullrich, *Photochem. Photobiol.*, 1996, 64(2) 254-58 teaches that UVB exposure activates IL-10 secretion, which depresses the function of Th1 cells, while enhancing the activity of Th2 cells. Magee, *Transplantation*, 47(6) 1008-1013, June 1989, reports the suppression of the elicitation of the immune response to alloantigen by UVB radiation, and concluded that the mechanism of suppression appears to be the induction of antigen-specific suppressor cells. Magee hypothesized that the suppression reported is due either to suppressor cells inhibiting T helper cell function, or to an inability of effector cells to proliferate in response to the antigenic stimulation. Magee concluded that UV-resistant antigen-presenting cells preferentially present antigen to T suppressor cell precursors, thus activating the suppressor cell arm of the immune response.

Ullrich, *Transplantation*, 46(1), July 1998, 115-119, investigated UV mediation of allograft rejection and concluded that alloantigenic sensitization of UV-irradiated mice induces suppressor T cells that are inhibiting the immune response against the alloantigen. Ullrich further noted the possibility that UVB alters the ability of antigen-presenting cells to activate helper cells—and at the same time, activates a UVB-resistant antigen-presenting cell that induces suppressor cells.

In one report relating specifically to UVB irradiation of the nasal mucosa, Csoma, *J. Photochem. Photobiol. B; Biology* 75(2004) 137-144 reports that UVB irradiation of the nasal passage significantly improved allergic rhinitis by significantly inhibiting rhinorrhoea, sneezing and nasal obstruction. Csoma noted that UVB irradiation has been shown to exert both local and systemic immunosuppression via a reduction in the number of Langerhans cells, increases in the production of immunosuppressive cytokines in macrophages, the induction of apoptosis in the T cells, in activated mast cells and eosinophils. Csoma further hypothesized that mechanisms of the effector phase of the immune response could be influenced by UVB radiation. Finally, Csoma noted that UV radiation has been shown to be able to induce antigen-dependent specific tolerance to a given antigen, but concluded that whether a similar antigen-dependent specific tolerance might be induced in patients by irradiation of the nasal mucosa with UVB light during exposure to the allergen is not known.

Other mechanisms by which UVB light induces immunosuppression have been reported in the literature. One hypothesis proposes that UVB radiation induces damage to nerve endings, thereby causing the release of CGRP, which causes the release of IL-10 and TNF-β from degranulating mast cells, thereby causing immunosuppression. Another hypothesis involves the release of α-MSH by keratinocytes.

Thus, it is believed that UVB irradiation of the NALT may act as a mucosal adjuvant and enhance down-regulatory Th2 immune responses to the antigen given via the mucosal surfaces.

Therefore, in accordance with the present invention, there is provided a method of inducing tolerance to an antigen in a mammal, comprising the steps of:
 a) irradiating mucosal associated lymphatic tissue (MALT) in the mammal with an effective amount of UV light, and
 b) mucosally administering an effective amount of the antigen to the mammal.

In some embodiments, the present invention provides co-administration in vivo or stimulation of an effective amount of autoantigen and TGF-β to nasal associated lymphatic tissue (NALT) in a patient.

The literature has reported that TGF-β can help polarize the immune response towards a Th2 phenotype. Liu, *Nature Immunology*, 2(7), July 2001, 585-589 reports that TGF-β stimulates immature dendritic cells to induce Th2 differentiation and/or inhibit Th1 differentiation. King, *Immunity*, Vol. 8, May 1998, 601-613 reports that 1 ng/ml TGF-β alters the preference of antigen presenting cells (APC), polarizing the antigenic response towards a Th2 phenotype.

Therefore, in accordance with the present invention, there is provided method of inducing tolerance to an antigen in a mammal, comprising the steps of:
 a) mucosally administering a formulation comprising an effective amount of the antigen and TGF-β to the mammal.

In some embodiments, the present invention provides co-administration of an effective amount of autoantigen and prostaglandin (PGE$_2$) to nasal associated lymphatic tissue (NALT) in a patient.

The literature has reported that PGE$_2$ can help polarize the immune response towards a Th2 phenotype. Liu, *Nature Immunology*, 2(7), July 2001, 585-589 reports that PGE2 stimulates immature dendritic cells to induce Th2 differentiation and/or inhibit Th2 differentiation.

Therefore, in accordance with the present invention, there is provided method of inducing tolerance to an antigen in a mammal, comprising the steps of:
 a) mucosally administering a formulation comprising an effective amount of the antigen and PGE$_2$ to the mammal.

In some embodiments, the present invention provides co-administration of an effective amount of autoantigen and immature dendritic cells of myeloid monocyte lineage (DC1s) to nasal associated lymphatic tissue (NALT) in a patient.

The literature has reported that dendritic cells often play a critical role in directing the type of T cell immune response, and that their direction often depends upon the stage at which they are providing their effector function. In short, when DC1 dendritic cells are mature, they induce a Th1 phenotype. In contrast, when the DC1 dendritic cells are immature, they induce IL-10—producing CD4+ and CD8+ regulatory T cells.

Therefore, in accordance with the present invention, there is provided method of inducing tolerance to an antigen in a mammal, comprising the steps of:
 a) mucosally administering a formulation comprising an effective amount of the antigen and immature dendritic cells to the mammal.

In some embodiments, the present invention provides co-administration of an effective amount of autoantigen and alum to nasal associated lymphatic tissue (NALT) in a patient. Alum has been used as an adjuvant for many years in vaccinations as a means of provoking Th2 polarization of the immune response:

Mattson, *Scand. J. Immunol.*, 46, 619-24, 1997, studied collagen-induced arthritis development in DA rats after immunization with alum adsorbed to collagen type II. Mattson reported that such immunization treatments suppressed disease development both prophalactically and therapeutically. Mattson reported choosing alum as the adjuvant in order to evoke a Th2 profile, and concluded that such a change occurred because there was a significant increase in IL-4 production and in the IgG1 anti-CII antibody response. Mattson further concluded that it was probable that pretreatment with alum-collagen II primes the immune system to produce Th2 instead of a Th1 response to collagen/FIA immunization, which normally causes arthritis.

Brewer, *J. Immunology*, 1999, 163:6448-6454, reports that alum adjuvants can induce IL-4 production and a Th2 response even in the absence of IL-4 signaling in mice deficient in either Il-4a or Stat6.

Comoy, *International Immunology*, 9(4), 523-531, reports immunizing mice with parasitic or bacterial protein antigens in combination with different adjuvants and reported that immunization with either protein antigen in alum induced a strong Th2-associated antibody (IgG1) and cytokine (IL-4) response. Comoy concluded that contrasting cytokine profiles could be induced against the same antigen, depending upon the adjuvant employed.

Cribbs, *International Immunology*, 15(4), 505-514, immunized wild-type mice with AB antigen in four adjuvants including alum. Cribbs reported that whereas three of the adjuvants provoked a Th1 response, alum provoked a Th2 response. Cribbs concluded that the choice of adjuvant may be critical for the design of a safe and effective immunotherapy for Alzheimer's Disease.

Therefore, in accordance with the present invention, there is provided method of inducing tolerance to an antigen in a mammal, comprising the steps of:
a) nasally administering a formulation comprising an effective amount of the antigen and alum to the mammal.

DETAILED DESCRIPTION OF THE INVENTION

In some embodiments, the present invention involves UV irradiation of mucosa-associated lymphoid tissue (MALT). In some embodiments, the MALT is gut-associated lymphoid tissue (GALT). In some embodiments, the MALT is bronchial-associated lymphoid tissue (BALT). In some embodiments, the MALT is nasal associated lymphoid tissue (NALT).

When GALT is selected to be irradiated, it is preferred that Peyers Patches within the patient's small intestine be irradiated. This may be accomplished in some embodiments by entering the intestine with a probe having the appropriate UV light source. In other embodiments, the UV light source may be located within a swallowable capsule. In this embodiment, the capsule is swallowed and the UV light source is activated upon entering the small intestine. In preferred embodiments, the pill also comprises a camera adapted to take pictures of the small intestine. In some embodiments, the pill is further adapted to release the selected antigen upon entry into the small intestine. It is believed that UV irradiation of the GALT may be efficacious in treating Crohn's Disease.

When NALT is selected to be irradiated, it is preferred that at least one of the palatine tonsil, lingual tonsil, and nasopharyngeal tonsil (adenoids) is irradiated. Preferably, each of these tonsils (which collectively form the Waldeyer's ring) is irradiated. In some embodiments, at least adenoid tissue in the patient is irradiated.

In other embodiments, a portion of the nasal mucosa is irradiated. It is believed that the nasal mucosa is a desirous site for establishing the desired Th2/Th3 responses to the antigen because it contains relatively high levels of TGF-B and IL-10, cytokines that help local APCs provide tolerogenic signals to B cells. In this embodiment, the irradiated portion of the nasal mucosa need not contain NALT. Despite the absence of NALT, irradiation of the nasal mucosa will cause direct irradiation of local macrophages that function as APCs. These irradiated macrophages will change morphology. Migrate to the NALT and begin to present antigen to the local B cells in a manner directed towards eliciting antigen-specific T suppressor cells. In particular, it is believed that UVB irradiation of a portion of the nasal mucosa may exert both local and systemic immunosuppression via a reduction in the number of Langerhans cells, alteration in the function of APCs, increases in the production of immunosuppressive cytokines in macrophages, the induction of apoptosis in the T cells, in activated mast cells and eosinophils. Each of these changes will help elicit a more polarized Th2/Th3 response to the antigen.

Therefore, in accordance with the present invention, there is provided a method of inducing tolerance to an antigen in a mammal, comprising the steps of:
a) irradiating nasal lymphatic tissue in the patient with an effective amount of UV light to produce e-selectin in an amount sufficient to tolerize the mammal to e-selectin.

In preferred embodiments, the antigen to be administered to the MALT or nasal mucosa is selected so that it can not only elicit suppressor T-cells capable of releasing TGF-β, IL-4 or IL-10 but also target these suppressor T-cells to a location within the body where the destructive cells are found in high concentration. The preferred and most efficient target for the suppressor T-cells is the organ or tissue under immune attack in the particular autoimmune disease involved, as the destructive cells will be concentrated in the vicinity of that organ or tissue. Hence, it is preferred that the antigen (to which the suppressor T-cells are specific) be itself an antigen specific to the tissue or organ under attack. Thus, the antigen may be an administered antigen, an autoantigen induced in vivo, or preferably a non-disease inducing fragment or analog of an autoantigen.

As noted above, in bystander suppression, it is not necessary that these suppressor T-cells recognize the disease-contributing cells—all that is necessary is that both types of cells be in the same vicinity when the suppressing cytokines are released. Therefore, it is preferable to use an antigen that (a) has the ability to elicit T-cells that cause release of suppressive cytokines and (b) is itself specific to the tissue or organ under attack so that the suppressor T-cells that cause release of the suppressive cytokines will be directed to the same organ or tissue which is also a location where the disease-promoting cells are concentrated.

The antigens disclosed in U.S. Pat. No. 5,546,504 ("Weiner"), the specification of which is incorporated by reference herein in its entirety, may be used in accordance with the present invention. The antigens may but do not need to be autoantigens, i.e. they do not need to be the same antigen(s) that is (are) under attack by the disease-inducing cells.

Preferred antigens are now discussed below:

In some embodiments, the antigen is myelin basic protein. (MBP). It has been reported in the literature that nasal administration of an effective amount of MBP reduces the severity of stroke and multiple sclerosis. For example, Becker, *Stroke*, 2003, 34, 1809-15 reports that exposing the nasal mucosa to MBP results in tolerized lymphocytes in the circulatory system. Similarly, Stohlman, *J. Immunology*, 1999, 163:6338-44 reports that peripheral Th2 cells that were activated by MBP antigen was able to attenuate EAE by their secretion of IL-10.

In some embodiments, the MBP is provided intranasally in an amount of between 0.2 g to 10 g for a human adult. This dose is provided between about 3 and 10 times on a quasi-daily basis. When MBP is selected as the antigen, the methods described in U.S. Pat. No. 6,068,884 (Becker), the specification of which is incorporated by reference in its entirety, may be used.

In some embodiments, the antigen is myelin oligodendrocyte glycoprotein (MOG). It has been reported in the literature that nasal administration of an effective amount of MOG reduces the severity of stroke. For example, Frenkel, *J. Immunology*, 2004, 172, 6459-55 reports that IL-10 secreting CD4+ T cells induced by nasal MOG reduce injury after stroke.

In some embodiments, the antigen is an adhesion molecule. Preferably, the adhesion molecule is selected from the group consisting of e-selectin, p-selection, ICAM and VCAM.

In some preferred embodiments, the antigen is E-selectin. It has been reported in the literature that nasal administration of an effective amount of E-selectin may help prevent stroke. For example, Takeda, *Stroke*, 2002, 33, 2156-64 reports that nasal installation of E-selectin potently inhibited the development of ischemic and hemorrhagic strokes in spontaneously hypertensive stroke-prone rats.

In some embodiments, the e-selectin is provided intranasally in an amount of between 0.5 ug and 50 mg per administration, preferably between 5 ug and 5 mg. This dose is provided between about 3 and 10 times on a quasi-daily basis.

In some embodiments of the present invention, the e-selectin is produced in situ within the mucosal tissue. It has been reported in the literature that UVA or UVB radiation of endothelial cells results in the production of significant amounts of e-selectin. See, for example, Viac, Photodermatol. Photoimmunol. Photomed. 1997 June, 13(3) 103-8; Heckman, *Br. J. Dermatol.*, 1994, September, 131(3), 311-8(UVA); Schornagel, *J. Invest. Dermatol.*, 123, (2004) 202-6; Strickland, *J. Invest. Drermatol.*, 1997 May 108(5) 763-8; and Norris, *J. Invest. Dermatol.*, 96, 763-770 (1991) (UVB). It has also been reported in the literature that oxidation of endothelial cells results in the production of significant amounts of e-selectin. See, for example, Rahman, *Am. J. Physiol.* 275 (Lung Cell. Mol. Physiol. 19):L533-L544, 1998. Because nasal tissue contains a significant population of endothelial cells, it is believed that the UV irradiation of NALT will result in enough locally produced e-selectin to produce the beneficial tolerance reported by Takeda, supra.

In some embodiments, the antigen is β-amyloid protein (βAP). It has been reported in the literature that nasal administration of an effective amount of βAP reduces the amount of plaque burden, which may decrease the severity of Alzheimer's Disease. For example, Weiner, *Ann. Neurol.* 2000, 48, 567-79 reports that treating PDAPP mice with human synthetic peptide intranasally each week significantly decreased the cerebral AB plaque burden.

In some embodiments, the antigen is selected from the group consisting of a neuritogenic peptide of PNS myelin component P2, a neuritogenic peptide of PNS myelin component P0, and a ganglioside. These antigens are believed to be autoantigens involved in chronic inflammatory demyelinating polyneuropathy (CIDP) and acute inflammatory demyelinating polyneuropathy (Guillain-Barre syndrome). In some embodiments, a mixture of these autoantigens is used.

In some embodiments, the antigen is insulin or glutamic acid decarboxylase (GAD). It has been reported in the literature that nasal administration of an effective amount of insulin or GAD reduces the development of diabetes. For example, Maron, *J. Autoimmunity*, (1999), 12, 251-258, reports that nasal administration of an effective amount of insulin or GAD reduces the development of diabetes.

In some embodiments, the insulin or GAD is provided intranasally in an effective amount of between about 3 and 10 times on a quasi-daily basis.

In some embodiments, the antigen is collagen. Collagen has been implicated as the autoantigen involved in rheumatoid arthritis.

In some embodiments, the antigen is a Wear Particle. In general, "Wear Particles" includes a) actual wear particles produced from the articulation of two surfaces, and b) particles having a composition and particle size distribution substantially similar to actual wear particles produced from the articulation of two surfaces. For example, "Wear Particles" includes UHMWPE particles produced from a physiologic articulation of a UHMWPE acetabular cup and a prosthetic femoral head, and b) particles having a composition and particle size distribution substantially similar to actual wear particles produced from the physiologic articulation of a UHMWPE acetabular cup and a prosthetic femoral head so as to cause an osteolytic response.

In some embodiments, the Wear Particles are titanium or a titanium alloy. This will allow immunization for Wear Particles emanating from articulation surfaces comprising titanium. In some embodiments, the Wear Particles are cobalt-chrome. This will allow immunization for Wear Particles emanating from articulation surfaces comprising cobalt-chrome. In some embodiments, the Wear Particles are UHMWPE. This will allow immunization for Wear Particles emanating from articulation surfaces comprising UHMWPE, such as those in UHMWPE acetabular cups or tibial components. In some embodiments, the Wear Particles are PMMA. This will allow immunization for particles emanating from cemented surfaces.

In some embodiments, collagen is added to the Wear-Particle-containing formulation of the present invention. Collagen typically has a hydrophobic tail. It is believed that this tail of the added collagen will complex with the Wear Particles in the same manner that the patient's collagen complexes with wear particles produced from a prosthesis, and thereby change the presentation of the collagen to the immune system to provide novel epitopes to the immune system.

In some embodiments, at least two antigens are administered in combination.

In some embodiments, the light source has a spectral maximum in the range of the UVB components of the solar spectrum. Preferably, the light source has a spectral maximum in the range of less than about 380 nm, and is preferably between 280 nm and 320 nm. In some embodiments, the light source has a spectral maximum of between about 300 nm and 315 nm. In some embodiments, narrowband UVB having a maximum emission in the range of 310-315 nm is used.

In some embodiments, the UVB light source is situated to irradiate adjacent tissue with between about 0.02 $J/cm^2$ and 2 $J/cm^2$ energy. Without wishing to be tied to a theory, it is believed that light transmission in this energy range will be sufficient to activate the epidermal cells (such as keratinocytes) of the MALT. Shreedhar, *J. Immunol.*, 1998, 160, 3783-9 has reported using a light dose of 0.02 $J/cm^2$ in order to activate keratinocytes to produce IL-10. Schmitt, *J. Immunology*, 2000, 165:3162-7 has reported using a dose of 1.5 $J/cm^2$. Rivas, *J. Immun*, 149, 12, 1992, 3865-71 has reported using a dose of 0.02 $J/cm^2$. Therefore, it is believed that irradiating MALT with at least about 0.02 $J/cm^2$ of UVB radiation will induce the macrophages and keratinocytes therein to produce and emit IL-10.

In some embodiments, the light source is situated to produce an energy intensity at the cell surface of between 0.1 watts/$cm^2$ and 10 watts/$cm^2$. In some embodiments, the light source is situated to produce about 1 milliwatt/$cm^2$. This latter value has been reported by Ullrich to effectively irradiate a cell surface in an amount sufficient to produce IL-10.

In some embodiments of the present invention, UVB irradiation causes sufficient IL-10 production to produce a local IL-10 concentration of at least 0.1 ng/ml. Shreedhar, *J. Immunol.*, 1998, 260, 3783-9, reports producing 313 pg IL-10/ml by exposing keratinocytes to 0.02 $J/cm^2$ UVB light, while Kang, *J. Immunol.*, 1994, 153, 5256 reports producing 333 pg/ml in a supernatant from CD11b+ macrophages exposed to 4 MEDs of UV light.

In some embodiments of the present invention, UVB irradiation causes sufficient IL-10 production to produce a local IL-10 concentration of at least 1 ng/ml. Shreedhar, *J. Immunol.*, 1998, 260, 3783-9, reports producing about 1.7 ng/ml of Il-10 by exposing mice to 0.015 $J/cm^2$ of UV radiation and then injecting the mice with IgG.

In preferred embodiments, UVB irradiation is generally carried out repeatedly over a period of about two weeks, more preferably over about one week. Within the one week period of irradiation, the patient may be subjected to between about 3-7 daily doses of UVB.

In preferred embodiments, the UVB exposure is carried out prior to antigen instillation. In some embodiments, the UVB exposure is carried out in parallel with antigen instillation. In some embodiments, the UVB exposure may be carried out after antigen instillation. Magee, *Transplantation*, 47(6), 1008-1013, June 1989 reported that exposure of mice to UVB radiation 1, 3 and 5 days after the injection of an alloantigen can significantly suppress the delayed hypersensitivity response.

In some embodiments, an intranasal UVB device disclosed in US Published Patent Application Nos. 2004/0030368 (Kemeny I) and 2004/0204747 (Kemeny II), the specifications of which are incorporated by reference in their entireties, is selected for use as the probe for intranasally delivering the UVB light.

In preferred embodiments, the UV light radiates a portion of tissue to which the antigen was applied. In some preferred embodiments, UVB light radiates a portion of the NALT to which the antigen was applied. In some preferred embodiments, UVB light radiates a portion of the nasal mucosa to which the antigen was applied.

In some embodiments, the light source has a spectral maximum in the UVA range, and is between about 321 nm and about 380 nm. In some embodiments, the UVA light source is situated to irradiate adjacent tissue with between about 0.02 $J/cm^2$ and 100 $J/cm^2$ energy. When UVA is used, it is more preferred that the MALT site be irradiated with photoenergy in the ultraviolet wavelength range at a radiation dose level of from about 0.1 $J/cm^2$ to about 100 joules/$cm^2$. Preferably, the dose level is from about 5 to about 60 joules/$cm^2$ of blood surface.

In some embodiments, the UVA irradiation is combined with a photoactivatable agent. The photoactivatable agent is preferably any agent which is capable of cross-linking with DNA. The class of psoralens are examples of such agents. Preferred psoralens are amino-methyl-trimethyl-psoralen (AMT) and 8-methoxy psoralen (8-MOP), which may be administered orally. Additional agents may be photoactive pyrene and monoclonal antibodies which have been linked to porphyrin molecules. The optimal wavelength range for activation of 8-MOP in T cells is 334-346 nm. The activated cells may be exposed to UV radiation for a period of from about 1 hour to about 6 hours. Within the optimal wavelength range, an approximately 270 minute exposure to UVA is required to provide the average lymphocyte with 2 $J/cm^2$. Whens psoralens is selected, the methods described in U.S. Pat. No. 4,838,852 ("Edelson"), the specification of which is incorporated by reference in its entirety, may be used.

When TGF-β is selected to be co-administered with the selected antigen, the dose of TGF-β should be in an amount effective to help polarize the immune response in the Th2 direction. In some embodiments, the TGF-β is provided in a concentration of between 0.1 ng/ml and 10,000 ng/ml.

In some embodiments, the TGF-β is supplied exogenously, such as from a recombinant TGF-β protein. In others, the TGF-β is supplied autologously, such as from platelet releasate. It is believed that approximate concentration of TGF-β found in about 10 cc's of platelet releasate, based upon about $10^6$ platelets, is about 100 ng/ml. This concentration is provided in the context of a spinal bone graft, and is believed to be due to the dilution with PPP. Because an intranasal formulation is typically only about 1 cc, the TGF-β concentration realizable in a formulation derived from PRP is about 10× higher, or 1000 ng/ml.

In some embodiments, it may be beneficial to add only the TGF-β growth factor from the platelet releasate to the formulation. Accordingly, it has been observed that most of the growth factors present in platelet releasate can be bound by heparin, and then eluted with NaCl.

| Growth Factor | NaCl Strength | Source |
|---|---|---|
| IGF-I | No Binding | Ikezawa, Conn. Tiss. Res., 1997, 36(4) 309-319 |
| PDGF | 0.5 | Mangrulkar, Biol. Repro. 1995, September 52(3), 636-46 |
| EGF | 1.1* | Mangrulkar, Biol. Repro. 1995, September 52(3), 636-46 |
| VEGF | 0.5 | Sakurada, Jpn.J. Can. Res, 1996, November 87, (11), 1143-52 |
| TGF-β | 0.9-1.2 | McCaffrey, J. Cell. Phys. 1992, August, 152(2) 430-40 |

*EGF (6 kDa) is a much smaller molecule than the other listed growth factors (~25-35 kDa), and so is often separated from other growth factors via size exclusion filters.

Therefore, in some embodiments, the TGF-β is selectively isolated from platelet releasate and then combined with the predetermined antigen in a formulation.

When immature dendritic cells are selected to be co-administered with the selected antigen, they may be concentrated from the patient's blood in the manner described in Ossevoort, *J. Immunol. Methods* 155, (1992)101-111. Ossevoort reports further culturing the DCs to obtain even higher concentrations thereof.

When alum is selected as Th2-polarizer, it is typically present in the formulation in a concentration of between about 1 mg/ml and 5 mg/ml.

Throughout the present specification, reference is made to various model systems that have been developed for studying autoimmune diseases. For example, experimental autoimmune encephalomyelitis (EAE) has been studied in mice and other rodent species as a model for Multiple Sclerosis (MS). Those of ordinary skill in the art recognize that many of the potential immune therapies for MS are first tested in this animal model system. The disease is induced by immunization with myelin basic protein (MBP), myelin oligodendrocyte protein (MOG), or proteolipid protein (PLP) and an adjuvant (such as Complete Freund's Adjuvant, "CFA"). The antigen that is used to induce the disease is the autoantigen in the model. This treatment, with either antigen, induces either a monophasic or an exacerbating/remitting form of demyelinating disease (depending on the type and species of rodent and well-known details of induction). The induced disease has many of the characteristics of the autoimmune disease MS and serves as an animal model therefor. Furthermore, the successful treatment of EAE by oral tolerization, and the parallel success in decreasing the frequency of disease-inducing cells in humans, and, in many cases, ameliorating the symptoms of MS, using oral administration of myelin, validates the use of EAE as a model system for predicting the success of different oral tolerization regimens.

One or more of the above disclosed model systems may be employed to demonstrate the efficacy and improved treatment provided by the present invention. In fact, the animal models are particularly suitable for testing therapies involving bystander suppression, precisely because this suppression mechanism is antigen-nonspecific. In the case of oral tolerization, therefore, the suppression of symptoms obtained in the model is independent of many of the actual or potential differences between a human autoimmune disorder and an animal model therefor.

The above animal models can be thus used to demonstrate the successful use of the present invention. For example, a multiple sclerosis autoantigen, bovine myelin, orally administered to humans in a double-blind study conferred a considerable benefit to a significant patient subset (Weiner, H. et al. Science 259:1321-1324, 1993). In addition, rheumatoid arthritis symptoms, such as joint tenderness, AM stiffness, grip strength, etc., were successfully suppressed in humans receiving oral collagen (0.1-0.5 mg single dose daily). (Trentham, D. et al., Science 261:1727, 1993.) Finally, preliminary human trials with oral S-antigen showed encouraging results for uveoretinitis. Large scale human studies are presently being conducted for multiple sclerosis, uveoretinitis, rheumatoid arthritis and diabetes. The predictive value of animal models for oral tolerization treatment of autoimmune diseases is supported by these human clinical studies.

The tolerance induced by the antigens of this invention is dose-dependent over a broad range of dosages. However, there are minimum and maximum effective dosages. In other words, active suppression of the clinical and histological symptoms of an autoimmune disease occurs within a specific dosage range, which, however, varies from disease to disease, mammal to mammal, and antigen to antigen. For example, when the disease is PLP-induced EAE in mice, the suppressive dosage range when MBP is used as the antigen is from about 0.1 to about 1 mg/mouse/feeding (with feedings occurring about every other day e.g., 5-7 feedings over a 10-14-day period). A most preferred dosage is 0.25 mg/mouse/feeding. For suppression of the MBP induced disease in rats, the MBP suppressive dosage range is from about 0.5 to about 2 mg/rat/feeding and the most preferred dosage is 1 mg/rat/feeding. An effective dosage range for humans with MS, when MBP is used as the oral tolerizer, is between about 1 and about 100, preferably between about 1 and about 20 mg MBP per day (administered every day or on alternate days for a period of time ranging from several months to several years) with the optimum being between about 7 and 10 mg per day.

The following terms used in this disclosure shall have the meaning ascribed to them below:

(a) "Antigen" is a protein, protein fragment, peptide, glycoprotein, or any other immunogenic substance (i.e. a substance capable of eliciting an immune response) that (i) upon oral, enteral or nasal administration elicits suppressor T-cells that cause TGF-β or IL-10 to be released and thereby suppress cells that contribute to destruction of tissue during an autoimmune disease and even when the destructive cells are specific to a different immunogenic substance. Preferably, the suppressor T-cells elicited by the antigen will be targeted to the same tissue that is under attack during an autoimmune disease. The term therefore encompasses but is not limited to antigens capable of causing the foregoing release of TGF-β or IL-10 and specific to the tissue or organ under attack in said autoimmune disease. The term also encompasses autoantigens and fragments or analogs thereof that have the ability to elicit such T-cell suppressors upon oral or enteral administration or upon inhalation. Thus, the antigen is not coextensive with "autoantigen".

(b) "Bystander suppression" is suppression of cells that contribute to autoimmune destruction by the release of the TGF-β or IL-10, this release being in turn mediated by suppressor T-cells elicited by the ingestion or inhalation of an antigen and recruited to the site where cells contributing to autoimmune destruction are found. The result is downregulation of the specific autoimmune response.

(c) "Mammal" is defined herein as any organism having an immune system and being susceptible to an autoimmune disease.

(d) "Autoimmune disease" is defined herein as a malfunction of the immune system of mammals, including humans, in which the immune system fails to distinguish between foreign substances within the mammal and/or autologous tissues or substances and, as a result, treats autologous tissues and substances as if they were foreign and mounts an immune response against them.

(e) "Autoantigen" is any substance or a portion thereof normally found within a mammal that, in an abnormal situation, is no longer recognized as part of the mammal itself by the lymphocytes or antibodies of that mammal, and is therefore the primary target of attack by the immunoregulatory system as though it were a foreign substance. The term also includes antigenic substances which induce conditions having the characteristics of an autoimmune disease when administered to mammals.

(f) "Treatment" is intended to include both the prophylactic treatment to prevent an autoimmune disease (or to prevent the manifestation of clinical or subclinical, e.g., histological symptoms thereof), as well as the therapeutic suppression or alleviation of symptoms after the onset of such autoimmune disease.

(g) "Synergists" are defined herein as substances which augment or enhance the suppression of the clinical (and/or histological) manifestation of autoimmune diseases when administered orally or by inhalation in conjunction with the administration of a bystander antigen and/or an autoantigen. As used in the preceding sentence, and elsewhere in this specification, "in conjunction with" (also referred to herein as in association with) means before, substantially simultaneously with or after oral or aerosol administration of autoantigens and/or bystander antigens. Naturally, administration of the conjoined substance should not precede nor follow administration of the autoantigen or bystander antigen by so long an interval of time that the relevant effects of the substance administered first have worn off. Therefore, the synergists should be administered within about 24 hours before or after the autoantigen or bystander antigen, and preferably within about one hour.

(h) A disease having the "characteristics" or "symptoms" of a particular autoimmune disease refers to a spontaneous or induced disease state that presents with specific inflammation of the same organ or tissue as that afflicted in the autoimmune disease. An example of an induced state is EAE, a model for multiple sclerosis. An example of a spontaneous state is diabetes developed by NOD mice.

We claim:

1. A method of inducing tolerance to an antigen in a mammal, comprising the steps of:
   a) irradiating nasal associated lymphatic tissue (NALT) in the mammal with an effective amount of UV light, and
   b) nasally administering an effective amount of the antigen to the mammal, wherein the antigen is E-selectin administered in an amount effective to inhibit the development of ischemic and hemorrhagic stroke.

2. The method of claim 1 wherein the e-selectin is provided intranasally in an amount of between 0.5 µg and 50 mg per administration.

3. The method of claim 1 wherein the e-selectin is provided intranasally in an amount of between 5 µg and 5 mg per administration.

4. The method of claim 1 wherein the e-selectin is provided between about 3 and 10 times.

* * * * *